United States Patent
Shanley et al.

(10) Patent No.: US 7,208,011 B2
(45) Date of Patent: Apr. 24, 2007

(54) IMPLANTABLE MEDICAL DEVICE WITH DRUG FILLED HOLES

(75) Inventors: John F. Shanley, Redwood City, CA (US); Theodore L. Parker, Danville, CA (US)

(73) Assignee: Conor Medsystems, Inc., Menlo Park, CA (US)

( * ) Notice: Subject to any disclaimer, the term of this patent is extended or adjusted under 35 U.S.C. 154(b) by 24 days.

(21) Appl. No.: 10/253,020

(22) Filed: Sep. 23, 2002

(65) Prior Publication Data

US 2003/0068355 A1   Apr. 10, 2003

(51) Int. Cl.
*A61F 2/06* (2006.01)

(52) U.S. Cl. .................. 623/1.42; 623/1.44; 623/1.46; 427/2.24

(58) Field of Classification Search ............ 623/1.39, 623/1.4, 1.42–1.48, 1.15; 424/424–426; 427/2.24, 2.25
See application file for complete search history.

(56) References Cited

U.S. PATENT DOCUMENTS

| | | | |
|---|---|---|---|
| 3,657,744 A | 4/1972 | Ersek | |
| 4,300,244 A | 11/1981 | Bokros | |
| 4,531,936 A | 7/1985 | Gordon | |
| 4,542,025 A | 9/1985 | Tice et al. | |
| 4,580,568 A | 4/1986 | Gianturco | |
| 4,650,466 A | 3/1987 | Luther | |
| 4,733,665 A | 3/1988 | Palmaz | |
| 4,739,762 A | 4/1988 | Palmaz | |
| 4,776,337 A | 10/1988 | Palmaz | |
| 4,800,882 A | 1/1989 | Gianturco | |
| 4,824,436 A | 4/1989 | Wolinsky | |
| 4,834,755 A | 5/1989 | Silvestrini et al. | |
| 4,955,878 A | 9/1990 | See et al. | |
| 4,957,508 A | 9/1990 | Kaneko et al. | |
| 4,960,790 A | 10/1990 | Stella et al. | |
| 4,969,458 A | 11/1990 | Wiktor | |
| 4,989,601 A | 2/1991 | Marchosky et al. | |
| 4,990,155 A | 2/1991 | Wilkoff | |
| 4,994,071 A | 2/1991 | MacGregor | |
| 5,019,090 A | 5/1991 | Pinchuk | |
| 5,049,132 A | 9/1991 | Shaffer et al. | |
| 5,053,048 A | 10/1991 | Pinchuk | |
| 5,059,166 A | 10/1991 | Fischell et al. | |

(Continued)

FOREIGN PATENT DOCUMENTS

CA    2234787    10/1998

(Continued)

OTHER PUBLICATIONS

Amy C. Richards Grayson et al., "Multi-Pulse Drug Delivery From a Resorbable Polymeric Microchip Device". Nature Materials, vol. 2, Nov. 2003, pp. 767-770.

(Continued)

*Primary Examiner*—David H. Willse
*Assistant Examiner*—Javier G. Blanco
(74) *Attorney, Agent, or Firm*—Cindy A. Lynch (57) ABSTRACT

The present invention relates to implantable medical devices for delivery of therapeutic agents, such as drugs, to a patient. More particularly, the invention relates to a device having therapeutic agents protected by a protective layer that prevents or retards processes that deactivate or degrade the active agents.

21 Claims, 3 Drawing Sheets

U.S. PATENT DOCUMENTS

| | | |
|---|---|---|
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffamn et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,472,985 A | 12/1995 | Grainger et al. |
| 5,473,055 A | 12/1995 | Mongelli et al. |
| 5,523,092 A | 6/1996 | Hanson et al. |
| 5,534,287 A | 7/1996 | Lukic |
| 5,545,208 A | 8/1996 | Wolff et al. |
| 5,545,210 A | 8/1996 | Hess et al. |
| 5,545,569 A | 8/1996 | Grainger et al. |
| 5,551,954 A | 9/1996 | Buscemi et al. |
| 5,556,413 A | 9/1996 | Lam |
| 5,575,771 A | 11/1996 | Walinsky |
| 5,578,075 A | 11/1996 | Dayton |
| 5,593,434 A | 1/1997 | Williams |
| 5,595,722 A | 1/1997 | Grainger et al. |
| 5,599,844 A | 2/1997 | Grainger et al. |
| 5,605,696 A | 2/1997 | Eury et al. |
| 5,607,442 A | 3/1997 | Fischell et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,643,314 A | 7/1997 | Carpenter et al. |
| 5,665,591 A | 9/1997 | Sonenshein et al. |
| 5,667,764 A | 9/1997 | Kopia et al. |
| 5,674,278 A | 10/1997 | Boneau |
| 5,679,400 A | 10/1997 | Tuch |
| 5,697,971 A | 12/1997 | Fischell et al. |
| 5,707,385 A | 1/1998 | Williams |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,769,883 A | 6/1998 | Buscemi et al. |
| 5,770,609 A | 6/1998 | Grainger et al. |
| 5,773,479 A | 6/1998 | Grainger et al. |
| 5,776,181 A | 7/1998 | Lee et al. |
| 5,776,184 A | 7/1998 | Tuch |
| 5,797,898 A | 8/1998 | Santini et al. |
| 5,800,507 A | 9/1998 | Schwartz |
| 5,807,404 A | 9/1998 | Richter |
| 5,811,447 A | 9/1998 | Kunz et al. |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,008 A | 11/1998 | Berg et al. |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,922,020 A | 7/1999 | Klein et al. |
| 5,922,021 A | 7/1999 | Jang |
| 5,928,916 A | 7/1999 | Keogh |
| 5,935,506 A | 8/1999 | Schmitz et al. |
| 5,945,456 A | 8/1999 | Grainger et al. |
| 5,957,971 A | 9/1999 | Schwartz |
| 5,964,798 A | 10/1999 | Imran |
| 5,968,092 A | 10/1999 | Buscemi et al. |
| 5,972,027 A | 10/1999 | Johnson |
| 5,976,182 A | 11/1999 | Cox |
| 5,980,551 A | 11/1999 | Summers et al. |
| 5,980,972 A | 11/1999 | Ding |
| 5,981,568 A | 11/1999 | Kunz et al. |
| 5,984,957 A | 11/1999 | Laptewicz, Jr. et al. |
| 5,992,769 A | 11/1999 | Wise |
| 5,994,341 A | 11/1999 | Hunter et al. |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,071,305 A | 6/2000 | Brown et al. |
| 6,074,659 A | 6/2000 | Kunz et al. |
| 6,083,258 A | 7/2000 | Yadav |
| 6,087,479 A | 7/2000 | Stamler et al. |
| 6,096,070 A | 8/2000 | Ragheb et al. |
| 6,099,561 A | 8/2000 | Alt |
| 6,120,535 A | 9/2000 | McDonald et al. |
| 6,120,536 A | 9/2000 | Ding et al. |
| 6,120,847 A | 9/2000 | Yang et al. |
| 6,121,027 A | 9/2000 | Clapper et al. |
| 6,123,861 A | 9/2000 | Santini et al. |
| 6,140,127 A | 10/2000 | Sprague |
| 6,153,252 A | 11/2000 | Hossainy et al. |

| | | | | | | |
|---|---|---|---|---|---|---|
| 6,156,062 A | 12/2000 | McGuinness | | 6,730,116 B1 | 5/2004 | Wolinsky et al. |
| 6,159,488 A | 12/2000 | Nagler et al. | | 6,746,686 B2 | 6/2004 | Hughes et al. |
| 6,171,609 B1 | 1/2001 | Kunz | | 6,759,054 B2 | 7/2004 | Chen et al. |
| 6,174,326 B1 | 1/2001 | Kitaoka et al. | | 6,764,507 B2 | 7/2004 | Shanley et al. |
| 6,193,746 B1 | 2/2001 | Strecker | | 2001/0000802 A1 | 5/2001 | Soykan et al. |
| 6,206,914 B1 | 3/2001 | Soykan et al. | | 2001/0027340 A1 | 10/2001 | Wright et al. |
| 6,206,915 B1 | 3/2001 | Fagan et al. | | 2001/0029351 A1 | 10/2001 | Falotico et al. |
| 6,206,916 B1 | 3/2001 | Furst | | 2001/0034363 A1 | 10/2001 | Li et al. |
| 6,231,600 B1 | 5/2001 | Zhong | | 2001/0044648 A1 | 11/2001 | Wolinsky et al. |
| 6,239,118 B1 | 5/2001 | Schatz et al. | | 2001/0044652 A1 | 11/2001 | Moore |
| 6,240,616 B1 | 6/2001 | Yan | | 2002/0002400 A1 | 1/2002 | Drasler et al. |
| 6,241,762 B1 | 6/2001 | Shanley | | 2002/0005206 A1 | 1/2002 | Falotico et al. |
| 6,245,101 B1 | 6/2001 | Drasler et al. | | 2002/0007209 A1 | 1/2002 | Scheerder et al. |
| 6,249,952 B1 | 6/2001 | Ding | | 2002/0007213 A1 | 1/2002 | Falotico |
| 6,254,632 B1 | 7/2001 | Wu et al. | | 2002/0007214 A1 | 1/2002 | Falotico et al. |
| 6,268,390 B1 | 7/2001 | Kunz | | 2002/0007215 A1 | 1/2002 | Falotico et al. |
| 6,273,908 B1 | 8/2001 | Ndondo-Lay | | 2002/0016625 A1 | 2/2002 | Falotico et al. |
| 6,273,910 B1 | 8/2001 | Limon | | 2002/0022876 A1 | 2/2002 | Richter et al. |
| 6,273,913 B1 | 8/2001 | Wright et al. | | 2002/0038145 A1 | 3/2002 | Jang |
| 6,280,411 B1 | 8/2001 | Lennox | | 2002/0071902 A1 | 6/2002 | Ding et al. |
| 6,290,673 B1 | 9/2001 | Shanley | | 2002/0072511 A1 | 6/2002 | New et al. |
| 6,293,967 B1 | 9/2001 | Shanley | | 2002/0082679 A1 | 6/2002 | Sirhan et al. |
| 6,299,604 B1 | 10/2001 | Ragheb et al. | | 2002/0082680 A1 | 6/2002 | Shanley et al. |
| 6,306,166 B1 | 10/2001 | Barry et al. | | 2002/0082682 A1 | 6/2002 | Barclay et al. |
| 6,306,421 B1 | 10/2001 | Kunz et al. | | 2002/0094985 A1 | 7/2002 | Herrmann et al. |
| 6,309,414 B1 | 10/2001 | Rolando et al. | | 2002/0123801 A1 | 9/2002 | Pacetti et al. |
| 6,312,460 B2 | 11/2001 | Drasler et al. | | 2002/0127263 A1 | 9/2002 | Carlyle et al. |
| 6,358,556 B1 | 3/2002 | Ding et al. | | 2002/0142039 A1 | 10/2002 | Claude |
| 6,358,989 B1 | 3/2002 | Kunz et al. | | 2002/0155212 A1 | 10/2002 | Hossainy |
| 6,379,381 B1 | 4/2002 | Hossainy et al. | | 2003/0028243 A1 | 2/2003 | Bates et al. |
| 6,395,326 B1 | 5/2002 | Castro et al. | | 2003/0028244 A1 | 2/2003 | Bates et al. |
| 6,399,144 B2 | 6/2002 | Dinh et al. | | 2003/0036794 A1 | 2/2003 | Ragheb et al. |
| 6,403,635 B1 | 6/2002 | Kinsella et al. | | 2003/0050687 A1 | 3/2003 | Schwade et al. |
| 6,423,092 B2 | 7/2002 | Datta et al. | | 2003/0060877 A1 | 3/2003 | Falotico et al. |
| 6,429,232 B1 | 8/2002 | Kinsella et al. | | 2003/0068355 A1 | 4/2003 | Shanley et al. |
| 6,451,051 B2 | 9/2002 | Drasler et al. | | 2003/0077312 A1 | 4/2003 | Schmulewicz et al. |
| 6,475,237 B2 | 11/2002 | Drasler et al. | | 2003/0083646 A1 | 5/2003 | Sirhan et al. |
| 6,491,666 B1 | 12/2002 | Santini et al. | | 2003/0088307 A1 | 5/2003 | Shulze et al. |
| 6,491,938 B2 | 12/2002 | Kunz et al. | | 2003/0125800 A1 * | 7/2003 | Shulze et al. ............... 623/1.15 |
| 6,497,916 B1 | 12/2002 | Taylor et al. | | 2003/0157241 A1 | 8/2003 | Hossainy et al. |
| 6,500,859 B2 | 12/2002 | Kinsella et al. | | 2003/0181973 A1 | 9/2003 | Sahota |
| 6,503,954 B1 | 1/2003 | Bhat et al. | | 2003/0199970 A1 | 10/2003 | Shanley |
| 6,506,411 B2 | 1/2003 | Hunter et al. | | 2003/0204239 A1 | 10/2003 | Carlyle et al. |
| 6,506,437 B1 | 1/2003 | Harish et al. | | 2003/0216699 A1 | 11/2003 | Falotico |
| 6,515,009 B1 | 2/2003 | Kunz et al. | | 2004/0073296 A1 | 4/2004 | Epstein et al. |
| 6,537,256 B2 | 3/2003 | Santini et al. | | | | |
| 6,544,544 B2 | 4/2003 | Hunter et al. | | FOREIGN PATENT DOCUMENTS | | |
| 6,551,838 B2 | 4/2003 | Santini et al. | | | | |
| 6,558,733 B1 | 5/2003 | Hossainy et al. | | DE | 202 00 220 | 3/2002 |
| 6,562,065 B1 | 5/2003 | Shanley | | EP | 0 335 341 | 10/1989 |
| 6,569,441 B2 | 5/2003 | Kunz et al. | | EP | 0 375 520 | 6/1990 |
| 6,569,688 B2 | 5/2003 | Sivan et al. | | EP | 0 470 246 | 2/1992 |
| 6,572,642 B2 | 6/2003 | Rinaldi et al. | | EP | 0 470 569 | 2/1992 |
| 6,585,764 B2 | 7/2003 | Wright et al. | | EP | 0551182 | 7/1993 |
| 6,585,765 B1 | 7/2003 | Hossainy et al. | | EP | 0 566 245 | 10/1993 |
| 6,599,928 B2 | 7/2003 | Kunz et al. | | EP | 0 567 816 | 11/1993 |
| 6,613,084 B2 | 9/2003 | Yang | | EP | 0568310 | 11/1993 |
| 6,627,246 B2 | 9/2003 | Mehta et al. | | EP | 0604022 | 6/1994 |
| 6,638,302 B1 | 10/2003 | Curcio et al. | | EP | 0623354 | 11/1994 |
| 6,645,547 B1 | 11/2003 | Shekalim et al. | | EP | 0 627 226 | 12/1994 |
| 6,656,162 B2 * | 12/2003 | Santini et al. ............... 604/191 | | EP | 0 679 373 | 11/1995 |
| 6,660,034 B1 | 12/2003 | Mandrusov et al. | | EP | 0 706 376 | 4/1996 |
| 6,663,881 B2 | 12/2003 | Kunz et al. | | EP | 0711158 | 5/1996 |
| 6,673,385 B1 | 1/2004 | Ding et al. | | EP | 0716836 | 6/1996 |
| 6,682,545 B1 | 1/2004 | Kester | | EP | 0 734 698 | 10/1996 |
| 6,702,850 B1 | 3/2004 | Byun et al. | | EP | 0 747 069 | 12/1996 |
| 6,712,845 B2 | 3/2004 | Hossainy | | EP | 0752885 | 1/1997 |
| 6,713,119 B2 | 3/2004 | Hossainy et al. | | EP | 0 770 401 | 5/1997 |
| 6,716,444 B1 | 4/2004 | Castro et al. | | EP | 0797963 | 10/1997 |
| 6,719,881 B1 | 4/2004 | Hunter et al. | | EP | 0850651 | 7/1998 |
| 6,720,350 B2 | 4/2004 | Kunz et al. | | EP | 0294905 | 12/1998 |
| 6,723,373 B1 | 4/2004 | Narayanan et al. | | EP | 0 897 700 | 2/1999 |
| 6,730,064 B2 | 5/2004 | Ragheb et al. | | EP | 0 950 386 | 10/1999 |

| | | |
|---|---|---|
| EP | 1 132 058 | 9/2001 |
| EP | 1 172 074 | 1/2002 |
| EP | 1181943 | 2/2002 |
| EP | 1 223 305 | 7/2002 |
| EP | 1222941 | 7/2002 |
| EP | 1 236 478 | 9/2002 |
| FR | 2 764 794 | 12/1998 |
| WO | WO 9001969 | 3/1990 |
| WO | WO 90/13332 | 11/1990 |
| WO | WO 91/10424 | 7/1991 |
| WO | WO 91/11193 | 8/1991 |
| WO | WO 91/12779 | 9/1991 |
| WO | WO 9200747 | 1/1992 |
| WO | WO 92/12717 | 8/1992 |
| WO | WO 92/15286 | 9/1992 |
| WO | WO 93/06792 | 4/1993 |
| WO | WO 9311120 | 6/1993 |
| WO | WO 9407529 | 4/1994 |
| WO | WO 94/21308 | 9/1994 |
| WO | WO 94/24961 | 11/1994 |
| WO | WO 9424962 | 11/1994 |
| WO | WO 95/03036 | 2/1995 |
| WO | WO 95/03795 | 2/1995 |
| WO | WO 95/24908 | 9/1995 |
| WO | WO 96/03092 | 2/1996 |
| WO | WO 96/25176 | 8/1996 |
| WO | WO 96/29028 | 9/1996 |
| WO | WO 96/32907 | 10/1996 |
| WO | WO 97/04721 | 2/1997 |
| WO | WO 9710011 | 3/1997 |
| WO | WO 98/08566 | 3/1998 |
| WO | WO 98/18407 | 5/1998 |
| WO | WO 98/19628 | 5/1998 |
| WO | WO 98/23228 | 6/1998 |
| WO | WO 98/23244 | 6/1998 |
| WO | WO 98/36784 | 8/1998 |
| WO | WO 98/58600 | 12/1998 |
| WO | WO 99/15108 | 4/1999 |
| WO | WO 99/16386 | 4/1999 |
| WO | WO 99/16477 | 4/1999 |
| WO | WO 99/44536 | 9/1999 |
| WO | WO 99/49928 | 10/1999 |
| WO | WO 99/55396 | 11/1999 |
| WO | WO 00/10613 | 3/2000 |
| WO | WO 0010622 | 3/2000 |
| WO | WO 00/45744 | 8/2000 |
| WO | WO 00/69368 | 11/2000 |
| WO | WO 00/71054 | 11/2000 |
| WO | WO 01/17577 | 3/2001 |
| WO | WO 01/45862 | 6/2001 |
| WO | WO 01/49338 | 7/2001 |
| WO | WO 0152915 | 7/2001 |
| WO | WO 01/87376 | 11/2001 |
| WO | WO 02/17880 | 3/2002 |
| WO | WO 02/26281 | 4/2002 |
| WO | WO 0226162 | 4/2002 |
| WO | WO 0241931 | 5/2002 |
| WO | WO 02087586 | 11/2002 |
| WO | WO 03018083 | 3/2003 |
| WO | WO 04043510 | 5/2004 |
| WO | WO 04043511 | 5/2004 |

OTHER PUBLICATIONS

Jennifer L. West, "Drug Delivery—Pulsed Polymers". Nature Materials, vol. 2, Nov. 2003, pp. 709-710.

Emanelsson, H. et al., *The Jostent® Coronary Stent Range*, Chapter 19.

Hwang, C-W. Et al., "*Physiological Transport Forces Govern Drug Distribution for Stent Based Delivery*", Circulation, (Aug. 17, 2001), pp. 1-8.

Bonnie L. Hiatt, et al. "The Drug-Eluting Stent: Is It the Holy Grail?" Reviews in Cardiovascular Medicine. (2001) vol. 2, No. 4, pp. 190-196.

Chao-Wei Hwang, et al. "Physiological Transport Forces Govern Drug Distribution for Stent-Based Delivery", Havard-MIT, Divsion of Health Sciences and Technology, Basic Science Reports, Circulation Aug. 7, 2001, pp. 1-8.

Ran Kornowski, et al. (Washington Hospital, Wash. D.C.); "Slow-Release Taxol Coated GR11 Stents Reduce Neointima Formation in a Porcine Coronary in-Stent Restenosis Model"; Abstract from the American Heart Association's 70th Scientific Sessions (Nov. 9-12, 1997).

Patrick W. Serruys, et al., "Heparin-Coated Palmaz-Schatz Stents in Human Coronary Arteries" Circulation, 1996; 93:412-422.

* cited by examiner

IMPLANTABLE MEDICAL DEVICE WITH DRUG FILLED HOLES

FIELD OF THE INVENTION

The invention relates to a therapeutic agent delivery device for delivery of agents, such as drugs, to a patient, and more particularly, the invention relates to a device having therapeutic agents separated by a protective layer.

DESCRIPTION OF THE RELATED ART

Implantable medical devices are often used for delivery of a beneficial agent, such as a drug, to an organ or tissue in the body at a controlled delivery rate over an extended period of time. These devices may deliver agents to a wide variety of bodily systems to provide a wide variety of treatments.

One of the many implantable medical devices which have been used for local delivery of beneficial agents is the coronary stent. Coronary stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as stainless steel, gold, silver, tantalum, titanium, and shape memory alloys, such as Nitinol.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. Despite the introduction of improved surgical techniques, devices, and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

One of the techniques under development to address the problem of restenosis is the use of surface coatings of various beneficial agents on stents. U.S. Pat. No. 5,716,981, for example, discloses a stent that is surface-coated with a composition comprising a polymer carrier and paclitaxel (a well-known compound that is commonly used in the treatment of cancerous tumors). The patent offers detailed descriptions of methods for coating stent surfaces, such as spraying and dipping, as well as the desired character of the coating itself: it should "coat the stent smoothly and evenly" and "provide a uniform, predictable, prolonged release of the anti-angiogenic factor." Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue.

Increasing the thickness of the surface coating has the beneficial effects of improving drug release kinetics including the ability to control drug release and to allow increased drug loading. However, the increased coating thickness results in increased overall thickness of the stent wall. This is undesirable for a number of reasons, including increased trauma to the vessel wall during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, duration of drug delivery, and the like that can be achieved.

In addition to sub-optimal release profiles, there are further problems with surface coated stents. The fixed matrix polymer carriers frequently used in the device coatings typically retain approximately 30% of the beneficial agent in the coating indefinitely. Since these beneficial agents are frequently highly cytotoxic, sub-acute and chronic problems such as chronic inflammation, late thrombosis, and late or incomplete healing of the vessel wall may occur. Additionally, the carrier polymers themselves are often highly inflammatory to the tissue of the vessel wall. On the other hand, use of biodegradable polymer carriers on stent surfaces can result in the creation of "virtual spaces" or voids between the stent and tissue of the vessel wall after the polymer carrier has degraded, which permits differential motion between the stent and adjacent tissue. Resulting problems include micro-abrasion and inflammation, stent drift, and failure to re-endothelialize the vessel wall.

Another significant problem is that expansion of the stent may stress the overlying polymeric coating causing the coating to plastically deform or even to rupture, which may therefore effect drug release kinetics or have other untoward effects. Further, expansion of such a coated stent in an atherosclerotic blood vessel will place circumferential shear forces on the polymeric coating, which may cause the coating to separate from the underlying stent surface. Such separation may again have untoward effects including embolization of coating fragments causing vascular obstruction.

In addition, it is not currently possible to deliver some drugs with a surface coating due to sensitivity of the drugs to water, other compounds, or conditions in the body which degrade the drugs. For example, some drugs lose substantially all their activity when exposed to water for a period of time. When the desired treatment time is substantially longer than the half life of the drug in water the drug cannot be delivered by know coatings. Other drugs, such as protein or peptide based therapeutic agents, lose activity when exposed to enzymes, pH changes, or other environmental conditions. These drugs which are sensitive to compounds or conditions in the body often cannot be delivered using surface coatings.

Accordingly, it would be desirable to provide a beneficial agent delivery device for delivery of agents, such as drugs, to a patient while protecting the agent from compounds or conditions in the body which would degrade the agent.

SUMMARY OF THE INVENTION

The present invention relates to medical device for delivery of therapeutic agents where the therapeutic agents are protected from degradation by a protective layer.

In one aspect the present invention is directed to an implantable medical device comprising an implantable device body having a plurality of holes therein; a therapeutic agent contained within the plurality of holes in the device body; and a protective layer of material provided in the plurality of holes and arranged to protect the therapeutic agent from compounds or conditions in the body which would degrade the agent. In a preferred embodiment the implantable medical device is a stent.

In preferred embodiments, the protective layer is a pharmaceutically acceptable bioerodible matrix that allows said therapeutic agent to be released as the matrix erodes.

In another preferred embodiment, the therapeutic agent is a first therapeutic agent provided in a first therapeutic agent layer adjacent said protective layer and said protective layer is a bioerodible matrix that prevents the therapeutic agent from being released until the protective layer has substantially eroded.

In yet another preferred embodiment, the implantable medical device further comprises a second therapeutic agent provided in a second therapeutic agent layer, wherein said protective layer separates the first therapeutic agent layer from a second therapeutic agent layer, and said first and second therapeutic agent layers each comprising a therapeutic agent disposed in a pharmaceutically acceptable bioerodible matrix.

Preferably the bioerodible matrix comprises pharmaceutically acceptable polymers, that may be selected from the group consisting of polylactic acid, polyglycolic acid, polylactic-co-glycolic acid, polylactic acid-co-caprolactone, polyethylene glycol, polyethylene oxide, polyvinyl pyrrolidone, polyorthoesters, polysaccharides, polysaccharide derivatives, polyhyaluronic acid, polyalginic acid, chitin, chitosan, cellulose, hydroxyehtylcellulose, hydroxypropylcellulose, carboxymethylcellulose, polypeptides, polylysine, polyglutamic acid, albumin, polyanhydrides, polyhydroxy alkonoates, polyhydroxy valerate, polyhydroxy butyrate, proteins, and polyphosphate esters.

Alternatively, the bioerodible matrix is selected from the group consisting of phosphatidylcholine, phosphatidylethanolamine, phosphatidylserine, sphingomyelin, dimyristoyl phosphatidylcholine, dipalmitoyl phosphatidylcholine, distearoyl phosphatidylcholine, distearoyl phosphatidylglycerol, dipalmitoyl phosphatidyl-glycerol, dimyristoyl phosphatidylserine, distearoyl phosphatidylserine, dipalmitoyl phosphatidylserine, fatty acids, and fatty acid esters.

In a preferred embodiment, the bioerodible matrix further comprises additives for controlling the rate of erosion.

In another preferred embodiment, the bioerodible matrix substantially prevents the ingress of water or enzymes.

Preferably the bioerodible matrix erodes by hydrolysis, dissolution, or enzymatic degradation. Alternatively, the protective layer erodes by physically breaking apart when the first therapeutic agent layer is substantially eroded.

In one embodiment, at least one therapeutic agent is homogeneously dispersed in said bioerodible matrix. In an alternative embodiment, the therapeutic agent is heterogeneously disposed in said bioerodible matrix, preferably as a solid particle dispersion, encapsulated agent dispersion, an emulsion, a suspension, a liposome, niosome, or a microparticle, wherein said niosome, liposome or microparticle comprise a homogeneous or heterogeneous mixture of the therapeutic agent.

In another preferred embodiment, the first and second therapeutic agents are homogeneously dispersed in each of said first and second therapeutic agent layers. Alternatively, the first and second therapeutic agents are heterogeneously disposed in each of said first and second therapeutic agent layers, preferably as a solid particle dispersion, encapsulated agent dispersion, and emulsion, a suspension, a liposome or a microparticle, wherein said liposome or microparticle comprise a homogeneous or heterogeneous mixture of the therapeutic agent.

Preferably, the therapeutic agent is selected from the group consisting of antineoplastic agents, neoplastic agents, antiproliferative agents, antisense compounds, immunosuppresants, angiogenic agents, angiogenic factors, antiangiogenic agents, and anti-inflammatory agents, or combinations thereof.

In still another preferred embodiment, the protective layer further comprises an activating or a deactivating agent, wherein the activating or deactivating agent prevents the loss of biological function of the first or second therapeutic agents, preferably the activating or deactivating agents are selected from the group consisting of antacids, buffers, enzyme inhibitors, hydrophobic additives, and adjuvants, more preferably the activating or deactivating agent is an antacid that protects one of said first and second therapeutic agents from a deactivating decrease in pH. Alternatively, the protective layer comprises an activating or deactivating agent that prevents deactivating interactions between said first and second therapeutic agents.

In one of its method aspects, the present invention is directed to a method for delivering a drug to a patient which method comprises placement within the patient's artery or vein of an implantable medical device as described above.

In another of its method aspects, the present invention is directed to a method for delivering a drug to a patient using an implantable medical device as described above, wherein said drug delivery method is used to treat restenosis in the patient after the patient has received percutaneous transluminal coronary angioplasty and intraluminal stent placement.

BRIEF DESCRIPTION OF THE DRAWING FIGURES

The invention will now be described in greater detail with reference to the preferred embodiments illustrated in the accompanying drawings, in which like elements bear like reference numerals, and wherein.

DETAILED DESCRIPTION OF THE INVENTION

The present invention relates to a beneficial agent delivery device for delivery of agents, such as drugs, to a patient. More particularly, the invention relates to a medical device having one or more therapeutic agents separated or protected from compounds or conditions within the body which would degrade the agent(s) by one or more protective layers.

First, the following terms, as used herein, shall have the following meanings:

The term "beneficial agent" as used herein are intended to have their broadest possible interpretation and is used to include any therapeutic agent or drug, as well as inactive agents such as barrier layers, carrier layers, therapeutic layers or protective layers.

The terms "drug" and "therapeutic agent" are used interchangeably to refer to any therapeutically active substance that is delivered to a bodily conduit of a living being to produce a desired, usually beneficial, effect. The present invention is particularly well suited for the delivery of antineoplastic, angiogenic factors, immuno-suppressants, and antiproliferatives (anti-restenosis agents) such as paclitaxel and Rapamycin for example, and antithrombins such as heparin, for example.

The therapeutic agents used in the present invention include classical low molecular weight therapeutic agents commonly referred to as drugs including all classes of action as exemplified by, but not limited to: antineoplastic, immuno-suppressants, antiproliferatives, antithrombins, antiplatelet, antilipid, anti-inflammatory, angiogenic, anti-angiogenic, vitamins, ACE inhibitors, vasoactive substances, antimitotics, metello-proteinase inhibitors, NO donors, estradiols, anti-sclerosing agents, alone or in combination. Therapeutic agent also includes higher molecular weight substances with drug like effects on target tissue sometimes called biologic agents including but not limited to: peptides, lipids, protein drugs, enzymes, oligonucleotides, ribozymes, genetic material, prions, virus, bacteria, and eucaryotic cells such as endothelial cells, monocyte/macrophages or vascular smooth muscle cells to name but a few examples. The therapeutic agent may also be a pro-drug, which metabolizes into the desired drug when administered to a host. In addition, the therapeutic agents may be preformulated as a microcapsules, microspheres, microbubbles, liposomes, niosomes, emulsions, dispersions or the like before it is incorporated into the therapeutic layer. The therapeutic agent may also be radioactive isotopes or agents activated by some other form of energy such as light or ultrasonic energy, or by other circulating molecules that can be systemically administered.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent, a therapeutic agent, an activating agent or a deactivating agent, as defined herein. A matrix is also a medium that may simply provide support, structural integrity or structural barriers. The matrix may be polymeric, non-polymeric, hydrophobic, hydrophilic, lipophilic, amphiphilic, and the like.

The term "bioerodible" refers to a matrix, as defined herein, that is bioresorbable and/or can be broken down by either chemical or physical process, upon interaction with a physiological environment. The bioerodible matrix is broken into components that are metabolizable or excretable, over a period of time from minutes to years, preferably less than one year, while maintaining any requisite structural integrity in that same time period.

The term "pharmaceutically acceptable" refers to a matrix or an additive, as defined herein, that is not toxic to the host or patient. When in reference to a matrix, it provides the appropriate storage and/or delivery of therapeutic, activating or deactivating agents, as defined herein, and does not interfere with the effectiveness or the biological activity of the agent.

The term "substantially eroded" refers to an erodable layer that has been broken down or absorbed into the system nearly completely. In a substantially eroded layer, at least about 75% of the original layer is eroded away, preferably, 90% of the material is eroded and more preferably 95% of the material is eroded away.

The term "substantially prevents or retards", as used in herein, refers to a process, such as water absorption, that is nearly stopped, but is probably not completely stopped from occurring. For this example, water absorption is substantially prevented if the rate at which water is absorbed is decreased by at least about 10%, more preferably by at least about 20% and even more preferably by at least about 50%, when compared to a standard.

The term "protective layer" refers to a matrix which serves to prevent or retard the occurrence of any process that would act to degrade or deactivate a drug, which is either contained in the same layer, or is contained in another adjacent layer. The protective layer is preferably bioerodible.

The term "erosion" refers to the process by which the components of a medium or matrix are bioresorbed and/or degraded and/or broken down by either chemical or physical process. For example in reference to polymers, erosion can occur by cleavage or hydrolysis of the polymer chains, such that the molecular weight of the polymer is lowered. The polymer of lower molecular weight will have greater solubility in water and is therefore dissolved away. In another example, erosion occurs by physically breaking apart upon interaction with a physiological environment.

The term "erosion rate" is a measure of the amount of time it takes for the erosion process to occur and is usually report in unit area per unit time.

The term "degrade" or "deactivate" refers to any process that causes an active component, such as a therapeutic agent, to become unable, or less able, to perform the action which it was intended to perform when incorporated in the device.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semi-synthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000. Examples of polymers include but are not limited to, poly-α-hydroxy acid esters such as, polylactic acid, polyglycolic acid, polylactic-co-glycolic acid, polylactic acid-co-caprolactone; polyethylene glycol and polyethylene oxide, polyvinyl pyrrolidone, polyorthoesters; polysaccharides and polysaccharide derivatives such as polyhyaluronic acid, polyalginic acid, chitin, chitosan, cellulose, hydroxyehtylcellulose, hydroxypropylcellulose, carboxymethylcellulose; polypeptides, and proteins such as polylysine, polyglutamic acid, albumin; polyanhydrides; polyhydroxy alkonoates such as polyhydroxy valerate, polyhydroxy butyrate, and the like.

The term "lipid", as used herein, refers to a matrix that comprises preferably non-polymeric small organic, synthetic or naturally-occurring, compounds which are generally amphipathic and biocompatible. The lipids typically comprise a hydrophilic component and a hydrophobic component. Exemplary lipids include, for example, fatty acids, fatty acid esters, neutral fats, phospholipids, glycolipids, aliphatic alcohols, waxes, terpenes, steroids and surfactants. Term lipid is also meant to include derivatives of lipids. More specifically the term lipids includes but is not limited to phosphatidylcholine, phosphatidylethanolamine, phosphatidylserine, sphingomyelin as well as synthetic phospholipids such as dimyristoyl phosphatidylcholine, dipalmitoyl phosphatidylcholine, distearoyl phosphatidylcholine, distearoyl phosphatidylglycerol, dipalmitoyl phosphatidylglycerol, dimyristoyl phosphatidylserine, distearoyl phosphatidylserine and dipalmitoyl phosphatidylserine.

The term "hydrogel" refers to cross-linked polymeric material in which the liquid component is water. Hydrogels may be prepared by cross-linking certain polymers and lipids disclosed herein.

The term "additives" refers to pharmaceutically acceptable compounds, materials, and compositions that may be included in a matrix along with a therapeutic agent. An additive may be encapsulated in or on or around a matrix. It may be homogeneously or heterogeneously disposed, as defined herein, in the matrix. Some examples of additives are pharmaceutically acceptable excipients, adjuvants, carriers, antioxidants, preservatives, buffers, antacids, and the like, such as those disclosed in Remington: The Science and Practice of Pharmacy, Gennaro, ed., Mack Publishing Co., Easton, Pa., 19th ed., 1995.

The term "holes" refers to holes of any shape and includes both through-openings and recesses.

The term "reaction environment" or "environment" refers to the area between a tissue surface abutting the device and the first intact layer of beneficial agent within a hole in the medical device.

The term "activating and deactivating agents" refers to a compound or material or medium that serves to prepare a reaction medium or environment for an active component. This may include the process of activating a compound (for example an enzyme) within the reaction environment. It may also include altering the pH or other physiological condition of the environment. This may further include the process of degrading a compound from the reaction environment or preventing deactivation or degradation. Some examples of activating and deactivating agents include, but are not limited to inorganic and organic acids and bases, (preferably inorganic) buffers, RNAase, catalysts, kinases, and the like.

The term "homogeneously disposed" refers to a component which is mixed uniformly in a matrix in such a manner that the component is macroscopically indistinguishable from the matrix itself. An example of a homogeneously disposed component is a drug formulation such as a microemulsion in which small beads of oil are dispersed uniformly in water.

The term "heterogeneously disposed" refers to a component which is mixed non-uniformly into a matrix in such a manner that the component is macroscopically distinguishable from the matrix itself. An example of a heterogeneously disposed component is a simple emulsion in which the beads of oil in the water are large enough to cause a turbidity to the solution and can be seen settling out of solution over time. Heterogeneously disposed compositions also include encapsulated formulations where a component, such as a protective layer, is layered onto or around a therapeutic agent or a therapeutic layer, forming a protective shell.

Implantable Medical Devices with Holes

Figures 1, 2:
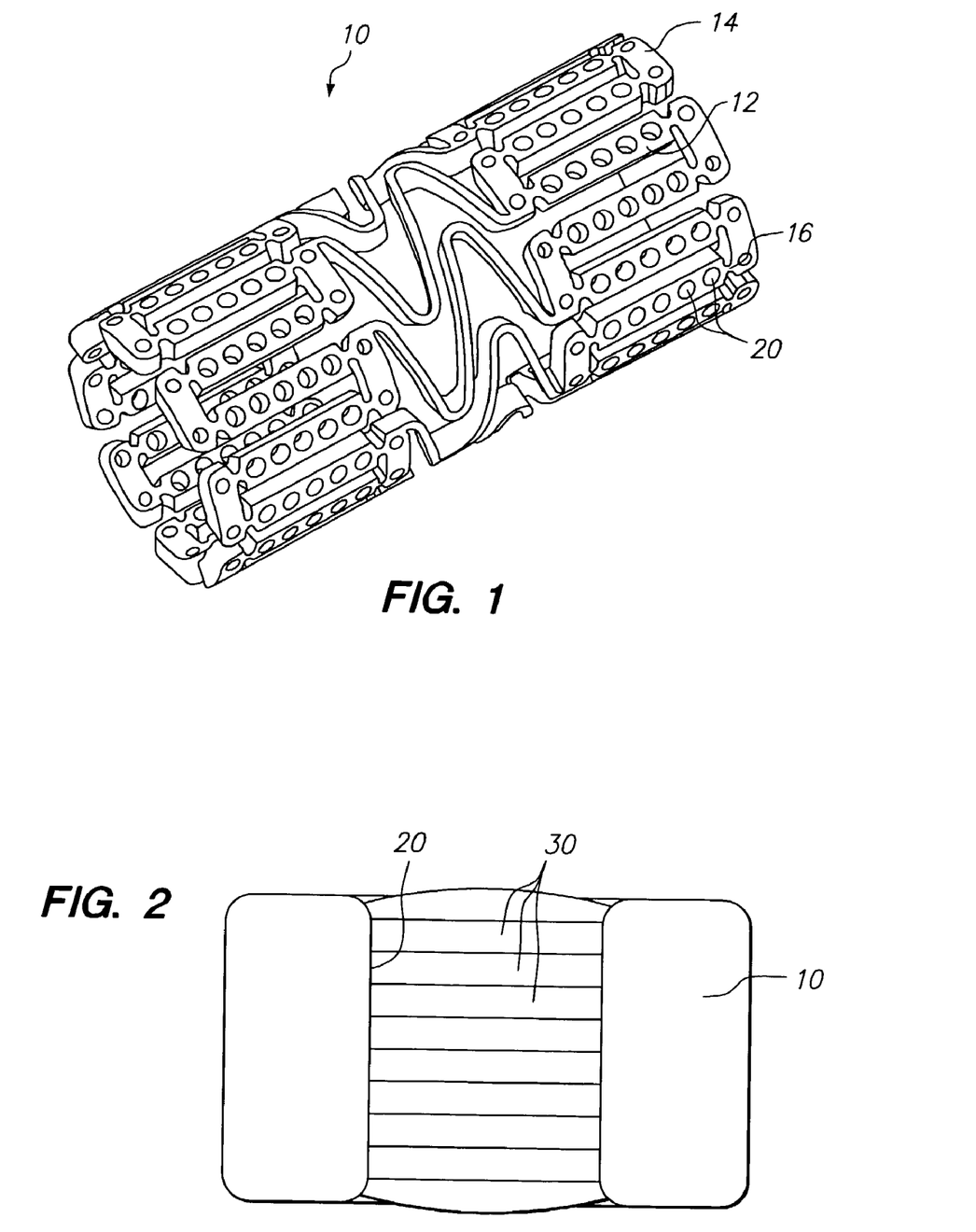
FIG. 1 is a perspective view of a therapeutic agent delivery device in the form of an expandable stent.
FIG. 2 is a cross sectional view of a portion of a therapeutic agent delivery device having a beneficial agent contained in an opening in layers.

FIG. 1 illustrates a medical device 10 according to the present invention in the form of a stent design with large, non-deforming struts 12 and links 14, which can contain holes 20 without compromising the mechanical properties of the struts or links, or the device as a whole. The non-deforming struts 12 and links 14 may be achieved by the use of ductile hinges 16 which are described in detail in U.S. Pat. No. 6,241,762 which is incorporated hereby by reference in its entirety. The holes 20 serve as large, protected reservoirs for delivering various beneficial agents to the device implantation site.

The relatively large, protected openings 20, as described above, make the expandable medical device of the present invention particularly suitable for delivering larger molecules or genetic or cellular agents, such as, for example, protein drugs, enzymes, antibodies, antisense oligonucleotides, ribozymes, gene/vector constructs, and cells (including but not limited to cultures of a patient's own endothelial cells). Many of these types of agents are biodegradable or fragile, have a very short or no shelf life, must be prepared at the time of use, or cannot be pre-loaded into delivery devices such as stents during the manufacture thereof for some other reason. The large holes 20 in the expandable device of the present invention form protected areas or receptors to facilitate the loading of such an agent either at the time of use or prior to use, and to protect the agent from abrasion and extrusion during delivery and implantation.

The volume of beneficial agent that can be delivered using holes 20 is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs and to achieve clinical efficacy without the undesirable side-effects of more potent drugs, such as retarded healing of the endothelial layer.

Holes also decrease the surface area of the beneficial agent bearing compounds to which the vessel wall surface is exposed. For typical devices with beneficial agent openings, this exposure decreases by a factors ranging from about 6:1 to 8:1, by comparison with surface coated stents. This dramatically reduces the exposure of vessel wall tissue to polymer carriers and other agents that can cause inflammation, while simultaneously increasing the quantity of beneficial agent delivered, and improving control of release kinetics.

FIG. 2 shows a cross section of a medical device 10 in which one or more beneficial agents have been loaded into the opening 20 in discrete layers 30. Examples of some methods of creating such layers and arrangements of layers are described in U.S. patent application Ser. No. 09/948,989, filed on Sep. 7, 2001, which is incorporated herein by reference in its entirety.

According to one example, the total depth of the opening 20 is about 125 to about 140 microns, and the typical layer thickness would be about 2 to about 50 microns, preferably about 12 microns. Each typical layer is thus individually about twice as thick as the typical coating applied to surface-coated stents. There would be at least two and preferably about ten to twelve such layers in a typical opening, with a total beneficial agent thickness about 25 to 28 times greater than a typical surface coating. According to one preferred embodiment of the present invention, the openings have an area of at least $5 \times 10^{-6}$ square inches, and preferably at least $7 \times 10^{-6}$ square inches.

Since each layer is created independently, individual chemical compositions and pharmacokinetic properties can be imparted to each layer. Numerous useful arrangements of such layers can be formed, some of which will be described below. Each of the layers may include one or more agents in the same or different proportions from layer to layer. The layers may be solid, porous, or filled with other drugs or excipients.

Figure 3:
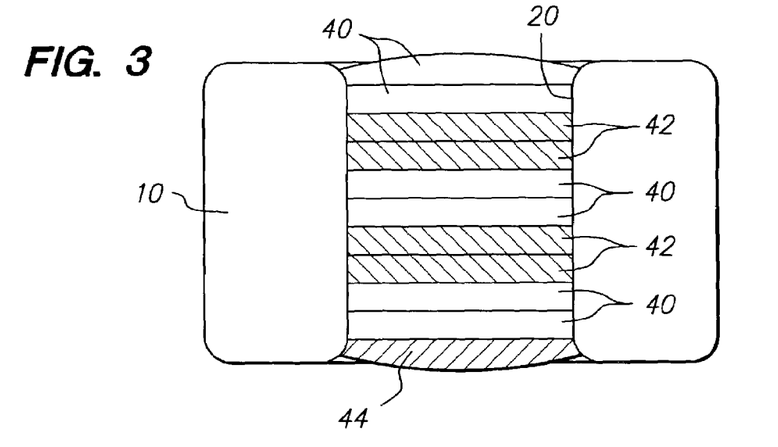
FIG. 3 is a cross sectional view of a portion of a therapeutic agent delivery device having therapeutic agent layers, protective layers, and a barrier layer contained in an opening in the device.

FIG. 3 shows an arrangement of layers provided in a through opening 20 in which layers 40 of a therapeutic agent in a biodegradable carrier material, are alternated with layers 42 of the biodegradable carrier material alone, with no active agent loaded, and a barrier layer 44 is provided at the inwardly facing surface. Such an arrangement releases therapeutic agent in three programmable bursts or waves achieving a stepped or pulsatile delivery profile. The use of carrier material layers without active agent creates the potential for synchronization of drug release with cellular biochemical processes for enhanced efficacy. The biodegradable carrier layers 42 and/or the barrier layer 44 may also be protective layers, as will be described below.

Alternatively, different layers could be comprised of different therapeutic agents altogether, creating the ability to release different therapeutic agents at different points in time. The layers of beneficial agent provide the ability to tailor a delivery profile to different applications. This allows the medical device according to the present invention to be used for delivery of different beneficial agents to a wide variety of locations in the body.

Figure 4:
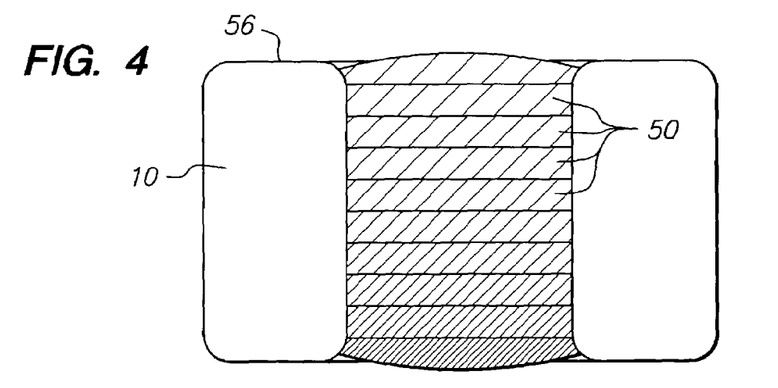
FIG. 4 is a cross sectional view of a portion of a therapeutic agent delivery device having beneficial agent layers having varying concentrations of therapeutic agent.

A further alternative is illustrated in FIG. 4. Here the concentration of the same therapeutic agent is varied from layer to layer, creating the ability to generate release profiles of arbitrary shape. Progressively increasing the concentration of agent in the layers 50 with increasing distance from the outwardly facing surface 56, for example, can produce a release profile with a constant release rate, also called a zero order release profile, which would be impossible to produce using known thin surface coating materials and techniques.

Certain types of drugs cannot be delivered by surface coatings or other known methods because of sensitivity of the drugs to compounds or conditions within the body which tend to degrade the drugs. For example, some drugs lose substantially all of their activity when exposed to water for a short period of time. Therefore, it is not possible to deliver these drugs over an extended period of time because the activity of the drug is substantially reduced by the time of delivery. Other drugs degrade in the presence of other compounds or conditions within the body including exposure to enzymes, pH changes, or other environmental conditions.

Figure 5:
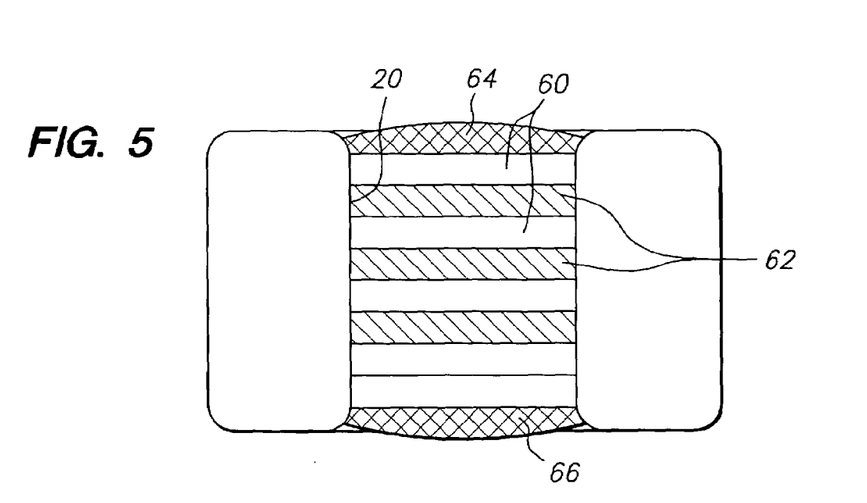
FIG. 5 is a cross sectional view of a portion of a therapeutic agent delivery device having therapeutic agent layers, protective layers, a barrier layer, and a cap layer contained in an opening in the device.

FIG. 5 illustrates an arrangement of layers of a therapeutic agent 60 layered between layers 62 of a protective material which protects the therapeutic agents from compounds or conditions within the body which would degrade the therapeutic agent. Examples of protective interlayers 62 will be discussed in detail below. FIG. 5 also illustrates a protective layer in the form of a cap layer 64 provided at a tissue contacting surface of medical device. The cap layer 64 blocks or retards biodegradation of subsequent layers and/or blocks or retards diffusion of the beneficial agent in that direction for a period of time which allows the delivery of the medical device to a desired location in the body. The barrier layer 64 may also function to prevent hydration of inner layers of beneficial agent and thus prevent swelling of the inner layers when such layers are formed of hygroscopic materials. FIG. 5 also illustrates a barrier layer 66. When the medical device 10 is a stent which is implanted in a lumen, the barrier layer 66 is positioned on a side of the opening 20 facing the inside of the lumen. The barrier layer 66 prevents the therapeutic agent 60 from passing into the lumen and being carried away without being delivered to the lumen tissue.

In the embodiment of FIG. 5, the protective layers 62 prevent or retard the flow of water (or other compounds) to the therapeutic layers 60 in a manner which will be described in further detail below. The protective layers 62 prevent or reduce the loss of biological function of the therapeutic agent by reducing contact of water with the therapeutic agent until a desired delivery time.

Figure 6:
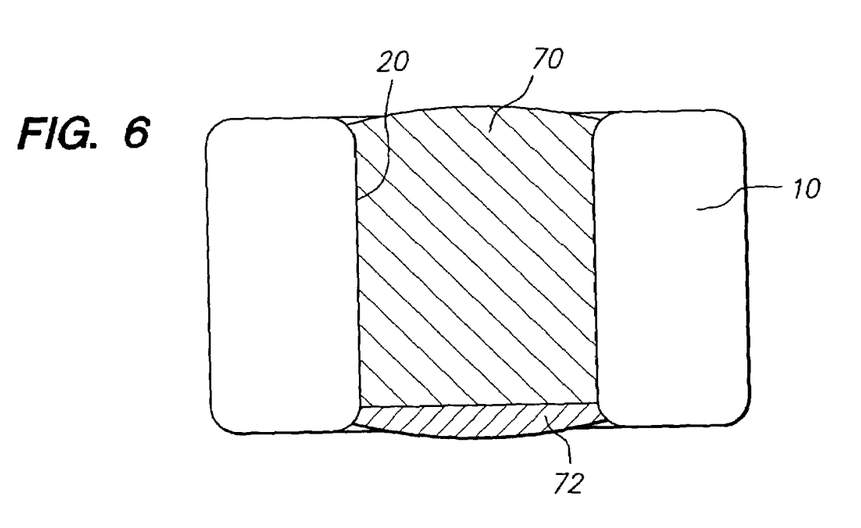
FIG. 6 is a cross sectional view of a portion of a therapeutic agent delivery device having a therapeutic agent and a protective material in a single layer and a separate cap layer.

FIG. 6 illustrates a further embodiment of the invention in which the opening 20 in the medical device 10 is filled with a therapeutic agent and a protective agent in the same layer or layers 70. In this embodiment, the therapeutic agent layer and the protective agent layer are incorporated in the same layer. Optionally, a barrier layers 72 may be provided as in the embodiment of FIG. 5.

Beneficial Agent Formulations

Beneficial agents include any therapeutic agent or drug, as well as inactive agents such as barrier layers, carrier layers, therapeutic layers or protective layers.

Therapeutic Layer Formulations

The therapeutic agent layers of the present invention are beneficial agents comprised of a matrix and at least one therapeutic agent. The matrix of the therapeutic agent layers can be made from pharmaceutically acceptable polymers, such as those typically used in medical devices. Such polymers are well known and include but are not limited to poly-α-hydroxy acid esters such as, polylactic acid, polyglycolic acid, polylactic-co-glycolic acid, polylactic acid-co-caprolactone; polyethylene glycol and polyethylene oxide; polyvinyl pyrrolidone; polyorthoesters; polysaccharides and polysaccharide derivatives such as polyhyaluronic acid, polyalginic acid, chitin, chitosan, cellulose, hydroxyethylcellulose, hydroxypropylcellulose, carboxymethylcellulose; polypeptides, and proteins such as polylysine, polyglutamic acid, albumin; polyanhydrides; polyhydroxy alkonoates such as polyhydroxy valerate, polyhydroxy butyrate, and the like, and copolymers thereof. The polymers and copolymers can be prepared by methods well known in the art (see, for example, Rempp and Merril: Polymer Synthesis, 1998, John Wiley and Sons) in or can be used as purchased from Alkermes, in Cambridge, Mass or Birmingham Polymer Inc., in Birmingham, Ala.

The preferred co-polymer for use in the present invention are poly(lactide-co-glycolide) (PLGA) polymers. The rate at which the polymer erodes is determined by the selection of the ratio of lactide to glycolide within the copolymer, the molecular weight of each polymer used, and the crystallinity of the polymers used.

Bioerodible polymers may also be used to form barrier layers that erode at a rate that can be predetermined based on the composition and that contain no therapeutic agent.

Additives in Protective layer and Therapeutic layer Formulations

Typical additives that may be included in a bioerodible matrix are well known to those skilled in the art (see Remington: The Science and Practice of Pharmacy, Gennaro, ed., Mack Publishing Co., Easton, Pa., 19th ed., 1995) and include but are not limited to pharmaceutically acceptable excipients, adjuvants, carriers, antioxidants, preservatives, buffers, antacids, emulsifiers, inert fillers, fragrances, thickeners, tackifiers, opacifiers, gelling agents, stabilizers, surfactants, emollients, coloring agents, and the like.

Typical formulations for therapeutic agents incorporated in these medical devices are well known to those skilled in the art and include but are not limited to solid particle dispersions, encapsulated agent dispersions, and emulsions, suspensions, liposomes or microparticles, wherein said liposome or microparticle comprise a homogeneous or heterogeneous mixture of the therapeutic agent.

The amount of the drug that is present in the device, and that is required to achieve a therapeutic effect, depends on many factors, such as the minimum necessary dosage of the particular drug, the condition to be treated, the chosen location of the inserted device, the actual compound administered, the age, weight, and response of the individual patient, the severity of the patient's symptoms, and the like.

The appropriate dosage level of the therapeutic agent, for more traditional routes of administration, are known to one skilled in the art. These conventional dosage levels correspond to the upper range of dosage levels for compositions, including a physiologically active substance and traditional penetration enhancer. However, because the delivery of the active substance occurs at the site where the drug is required, dosage levels significantly lower than a conventional dosage level may be used with success. Ultimately, the percentage of therapeutic agent in the composition is determined by the required effective dosage, the therapeutic activity of the particular formulation, and the desired release profile. In general, the active substance will be present in the composition in an amount from about 0.0001% to about 99%, more preferably about 0.01% to about 80% by weight of the total composition depending upon the particular substance employed. However, generally the amount will range from about 0.01% to about 75% by weight of the total composition, with levels of from about 25% to about 75% being preferred.

Protective Layer Formulations

The protective layers of the present invention are beneficial agents comprised of a bioerodible matrix and optionally contain additional additives, therapeutic agents, activating agents, deactivating agents, and the like. Either a property of the chosen material of the protective layer, or a chemical embedded in the protective layer provides protection from deactivating processes or conditions for at least one therapeutic agent. In addition to the polymer materials described above, the protective layer may also be comprised of pharmaceutically acceptable lipids or lipid derivatives, which are well known in the art and include but are not limited to fatty acids, fatty acid esters, lysolipids, phosphocholines, (Avanti Polar Lipids, Alabaster, Ala.), including 1-alkyl-2-acetoyl-sn-glycero 3-phosphocholines, and 1-alkyl-2-hydroxy-sn-glycero 3-phosphocholines; phosphatidylcholine with both saturated and unsaturated lipids, including dioleoylphosphatidylcholine; dimyristoyl-phosphatidylcholine; dipentadecanoylphosphatidylcholine; dilauroylphosphatidyl-choline; dipalmitoylphosphatidylcholine (DPPC); distearoylphosphatidylcholine (DSPC); and diarachidonylphosphatidylcholine (DAPC); phosphatidyl-ethanolamines, such as dioleoylphosphatidylethanolamine, dipahnitoyl-phosphatidylethanolamine (DPPE) and distearoylphosphatidyleffianolamine (DSPE); phosphatidylserine; phosphatidylglycerols, including distearoylphosphatidylglycerol (DSPG); phosphatidylinositol; sphingolipids such as sphingomyelin; glucolipids; sulfatides; glycosphingolipids; phosphatidic acids, such as dipahmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene-glycol (PEG), also referred to herein as "pegylated lipids", with preferred lipids bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyethylene fatty acid esters, polyoxyethylene fatty alcohols, polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oil, polyoxyethylene-polyoxypropylene polymers, and polyoxyethylene fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose acetate isobutyrate (SAIB), sucrose laurate, fructose laurate, sucrose palritate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol monolaurate, glycerol dipalmitate, glycerol and glycerol esters including glycerol tripalmitate, glycerol monopalmitate, glycerol distearate, glycerol tristearate, glycerol monostearate, glycerol monomyristate, glycerol dimyristate, glycerol trimyristate; long chain alcohols including n-decyl alcohol, lauryl alcohol, myristyl alcohol, cetyl alcohol, and n-octadecyl alcohol; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or combinations thereof.

If desired, a cationic lipid may be used, such as, for example, N-[1-(2,3-dioleoyloxy)propyl]-N, N ,N-trimethylammonium chloride (DOTMA), 1,2-dioleoyloxy-3-(trimethylammonio)propane (DOTAP); and 1,2-dioleoyl-3-(4'-trimethylammonio)butanoyl-sn-glycerol (DOTB). If a cationic lipid is employed in the lipid compositions, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

These lipid materials are well known in the art and can be used as purchased from Avanti, Burnaby, B.C. Canada.

The preferred lipids for use in the present invention are phosphatidyl-choline, phosphatidylethanolamine, phosphatidylserine, sphingomyelin as well as synthetic phospholipids such as dimyristoyl phosphatidylcholine, dipalmitoyl phosphatidylcholine, distearoyl phosphatidylcholine, distearoyl phosphatidyl-glycerol, dipalmitoyl phosphatidylglycerol, dimyristoyl phosphatidylserine, distearoyl phosphatidylserine and dipalmitoyl phosphatidylserine.

The rate at which the bioerodible matrix erodes is determined by the choice of lipid, the molecular weight, and the ratio of the chosen materials.

The protective layer can erode by either chemical or physical erosion mechanisms. If the layer erodes by a physical mechanism, the layer is typically a thin film from about 0.1 µm to about 3 µm of a non-polymeric material embedded between two polymeric layers. In this instance, the structural integrity of the protective layer is maintained by the presence of both of these polymeric layers. When the polymeric material closest to the luminal surface erodes away, the protective layer breaks apart by the physical forces exerted on it from the remaining polymeric layer. In another embodiment, the protective layer is eroded by chemical interactions, dissolution in water, hydrolysis, or reaction with enzymes.

One function of the protective layer is to protect one or more therapeutic agents from deactivating or degrading conditions. The protection may come from the properties of the material when, for example, a hydrophobic protective layer would protect a water sensitive agent from water by resisting the influx of moisture. The protective layer may also act as a physical barrier. For example, a protective layer comprised of a hydrogel may allow water to be absorbed by the gel, and allow any agents contained within the gel to diffuse out of the gel into the reaction environment. The hydrogel, however, would prevent enzymes from penetrating the layer, thereby protecting any agents contained within from the enzyme. Finally the protective layer does not have to act as a barrier. The protective layer may protect a therapeutic agent by releasing an agent, such as an activating agent or a deactivating agent, into the reaction environment prior to the release of the therapeutic agent.

A therapeutic agent may be incorporated directly in the protective layer. The therapeutic agent can be heterogeneously or homogeneously dispersed in the protective layer. The therapeutic agent can be a drug, or a drug formulated into a microcapsule, niosome, liposome, microbubble, microsphere, or the like. In addition, the protective layer may contain more than one therapeutic agent. For example, a water sensitive drugs, such as a limus, or any other drug that must be administered through intravenous, intramuscular, or subcutaneously, could be incorporated in a hydrophobic matrix such as SAIB, or fatty acid ester.

A therapeutic agent may also be disposed in a therapeutic agent layer, separate from the protective layer. In this case the protective layer may be adjacent to the therapeutic agent layer and may serve to prevent or retard processes that would degrade or deactivate the therapeutic agent until the protective layer has substantially eroded. In this instance the protective layer is a barrier between a therapeutic layer and the reaction environment. This barrier may be a hydrophobic barrier that resists water absorption. The hydrophobic barrier would be used in conjunction with water-sensitive drugs as described above. Alternatively, the protective layer maybe a hydrogel that resists the absorbance of enzymes. An enzyme resistant barrier would used to protect an drug such as a DNA, RNA, peptide or protein based therapeutic agent.

The protective layer may optionally include activating and deactivating agents for the purpose of preparing the reaction environment for the subsequent release of a therapeutic agent. These activating and deactivating agents are well known to those skilled in the art and include but are not limited to antacids, buffers, enzyme inhibitors, hydrophobic additives, and adjuvants. For example, $Mg(OH)_2$ in particles of about 0.5 µm to about 5 µm more preferably, about 1 µm incorporated in a PLGA polymer layer could be used in conjunction with any acid sensitive drug. An example of an activating agent is chymotrypsin, which may be incorporated in polyvinyl pyrrolidone layer. The chymotrypsin, could be used to convert a pro-drug to an active drug.

Preferred Embodiments

In one embodiment, the protective layer of the present invention is essentially hydrophobic and can prevent or retard the absorption of water. This is especially advantageous for the delivery of water sensitive drugs such as a limus. Some examples of hydrophobic, bioerodible matrix materials are lipids, fatty acid esters, such as glycerides. The erosion rate is controlled by varying the hydrophilic-lipophilic balance (HLB). Alternatively, the hydrophobic protective layer may encapsulate the therapeutic agent, and the encapsulated particles may be dispersed in either a polymer or lipid matrix.

In another embodiment, the protective layer may contain an antacid, or pH retaining agent, that protects a therapeutic agent from a deactivating reduction in pH. Polymers comprised of monomer units of lactide, glycolide, caprolactone, β-hydroxy valerate, trimethylene carbonate, dioxanone, β-hydroxy butyrate and other co-hydroxyalkyl carboxylic acids are degraded by water in hydrolysis in vivo and in vitro to produce free acid groups in such a quantity that the microclimate within the polymer matrix, and sometimes the external environment, becomes acidic with a pH of less than or equal to six during the process of polymer degradation. Some therapeutic agents that can be advantageously delivered in local, sustained fashion from such polymers are sensitive to an acidic environment in that their biological activity is attenuated or eliminated as the pH decreases during the polymer matrix degradation required to release the agent from the delivery matrix. Examples of such acid sensitive agents are RNA oligomers with phosphodiester-ribose linkages or morpholino-imidate linkages (so-called "anti-sense oligo's), limus's (like sirolimus and everolimus) and generally therapeutic agents that have chemical functionality that undergo acid catalyzed hydrolysis (such as ester, amide, urea, Spiro ester, anhydride and carbonate) or that contain functional groups that can be protonated at pH less than or equal to six to render the agent biologically inactive, such as amino and imino groups (such as the deactivation of bio-active proteins).

To mitigate the effects of acidity generated during polymer degradation and in vivo resorption, both within the matrix (the micro-climate) and outside the matrix (the environment), it is envisioned to include an acid scavenger, antacid or neutralization agent capable of maintaining the pH at equal to or greater than six or above a threshold pH where the particular agent become therapeutically ineffective. Inorganic antacids contemplated include metal hydroxides, particularly divalent metal hydroxides like Mg(OH)$_2$ and Ca(OH)$_2$ and Ba(OH)$_2$, monovalent bicarbonates and carbonates like NaHCO$_3$ and Na$_2$CO$_3$, divalent carbonates like ZnCO$_3$, monovalent and divalent hydrogen phosphates and dihydrogen phosphates like Na$_2$HPO$_4$ and Na$_2$HPO$_4$, monovalent salts of carboxylic acids, like sodium acetate. Additionally, organic bases such as organic amines are envisioned as acid scavengers, such as triethanol amine, ethanolamine, morpholine, pyrimidine and purine bases, poly ethyleneimine, nucleosides, amino acids and poly amino acids, particularly poly lysine and poly hydroxylysine, poly arginine and peptides containing lysine, hydroxy lysine, arginine and/or histidine units.

Inorganic antacids are contemplated to be incorporated into the polymer matrix by standard polymer processing techniques such as solvent casting, molding, blending, milling and extrusion. The amount of antacid will be enough to provide for acid neutralization during some or all of the time the acid sensitive agent or combination of agents are released in therapeutically relevant dosages and pharmacokinetic profiles. The antacid may be incorporated into the polymeric drug delivery matrix in amounts up to where the desired physical characteristics are compromised for the desired application, or may be used at lower levels. Antacids may be used alone or in combination with other antacids. For polymers containing lactide and/or glycolide (the so-called PLGA family of polymers), the amount of antacid will generally not exceed 10% by weight and may preferably be used at 1–6% by weight. The antacid need not be used at the stoichiometric level calculated for complete polymer degradation or hydrolysis, but may provide beneficial protection for the acid sensitive agents at less than stoichiometric values, particularly if all the agent is delivered prior to complete degradation of the polymer to its constituent monomer or co-monomer units.

In still another embodiment, the protective layer protects a therapeutic agent from a deactivating or degrading enzyme. An enzyme inhibitor can be incorporated into the protective layer, so that it is introduced to the reaction environment as the protective layer erodes. The therapeutic agent would then enter an environment with less enzyme than would be present if the inhibitor were not incorporated in the protective layer. Alternatively the protective layer may be made of a hydrogel material, such as calcium alginate, (made by adding Ca(OH)$_2$ to polyalginic acid) that allows small molecules to diffuse into and out of the gel, but substantially prevents larger molecules from entering the protective layer. DNA, RNA, peptide and protein based therapeutics would be protected using hydrogel barriers.

Uses for Implantable Medical Devices

Although the present invention has been describe with reference to a medical device in the form of a stent, the medical devices of the present invention can also be medical devices of other shapes useful for site-specific and time-release delivery of drugs to the body and other organs and tissues. The drugs may be delivered to the vasculature including the coronary and peripheral vessels for a variety of therapies, and to other lumens in the body. The drugs may increase lumen diameter, create occlusions, or deliver the drug for other reasons.

Medical devices and stents, as described herein, are useful for the prevention or amelioration of restenosis, particularly after percutaneous transluminal coronary angioplasty and intraluminal stent placement. In addition to the timed or sustained release of anti-restenosis agents, other agents such as anti-inflammatory agents may be incorporated in to the multi-layers incorporated in the plurality of holes within the device. This allows for site-specific treatment or prevention any complications routinely associated with stent placement that are known to occur at very specific times after the placement occurs.

The methods for loading beneficial agents into openings in an expandable medical device may include known techniques such as dipping and coating and also known piezo-electric micro-jetting techniques. Micro-injection devices may be used to deliver precise amounts of one or more liquid beneficial agents including protective layers, therapeutic agent layers, and any other layers to precise locations on the expandable medical device in a known manner. The beneficial agents may also be loaded by manual injection devices.

EXAMPLES

In the examples below, the following abbreviations have the following meanings. If an abbreviation is not defined, it has its generally accepted meaning.

mL = milliliters
M = Molar
wt. = weight
vol. = volume
μL = microliters
μm = micrometers
nm = nanometers
DMSO = Dimethyl sulfoxide'
NMP = N-methylpyrrolidone
DMAC = Dimethyl acetamide Example 1

Formulation Comprising a Therapeutic Agent within the Protective Layer

A first mixture of poly(lactide-co-glycolide) (PLGA) (Birmingham Polymers, Inc), lactide:glycolide: 85:15, ($M_v$>100,000 Daltons) 7% wt. and a suitable organic solvent, such as DMSO, NMP, or DMAC 93% wt. is prepared. The mixture is loaded dropwise into holes in the stent, then the solvent is evaporated to begin formation of the barrier layer. A second barrier layer is laid over the first by the same method of filling polymer solution into the hole followed by solvent evaporation. The process is continued until five individual layers have been laid down to form the barrier layer.

A second mixture of a limus, such as sirolimus, 3% solids basis, and dipalmitoyl phosphatidylcholine (DPPC), 7% solids basis, in a suitable organic solvent, such as DMSO, is introduced into holes in the stent over the barrier layer. The solvent is evaporated to form a drug filled protective layer and the filling and evaporation procedure repeated until the hole is filled to about 75% of its total volume with drug in protective layer layered on top of the barrier layer.

Three layers of a third solution, of poly(lactide-co-glycolide) (PLGA), lactide:glycolide: 50:50, ($M_v$≅80,000 Daltons) 7% wt. and a suitable organic solvent, such as DMSO, are then laid down over the drug in matrix layer to provide a cap layer.

Following implantation of the filled stent in vivo, the cap layer degrades allowing the limus to be delivered. The barrier layer prevents the therapeutic agent from being delivered out the barrier layer side of holes in the stent.

Example 2

Formulation Comprising Therapeutic Agents in Therapeutic Agent Layers and a Protective Layer Separating the Therapeutic Agent Layers

A first mixture of poly(lactide-co-glycolide) (PLGA), lactide:glycolide: 85:15, ($M_v$>100,000 Daltons) 7% wt. and a suitable organic solvent, such as DMSO, 93% wt. is prepared. The mixture is loaded drop-wise into holes in the stent, and the solvent is then evaporated to form the barrier layer. A second barrier layer is laid over the first by the same method of filling polymer solution into the hole followed by solvent evaporation. The process is continued until five individual layers have been laid down to form the barrier layer.

A second mixture of an PCN-1 ribozyme, 8% solids basis, and poly(vinylpyrrolidone) (PVP), molecular weight 8,000 daltons, 2% solids basis, in an mixed solvent of RNA-ase/DNA-ase free water, 50% vol., and dimethyl sulfoxide (DMSO), 50% vol., is introduced into holes in the stent over the barrier layer. The solvent is evaporated to form a therapeutic agent layer and the filling and evaporation procedure repeated until the hole is filled sufficiently.

Three layers of a third solution, SAIB, (Eastman Chemicals) 7% wt. and a suitable organic solvent, such as DMSO, are then laid down over the drug in matrix layer to provide a protective layer.

A fourth mixture of PLGA, lactide:glycolide: 50:50, ($M_v$≅80,000 Daltons) 5% wt., Dexamethasone, 5% wt., and a suitable organic solvent, such as DMSO, 90% wt. is prepared. The mixture is then loaded into the holes and the solvent is evaporated to form a second therapeutic agent layer. This process is continued until five layers have been laid down.

A fifth mixture of PLGA, lactide:glycolide: 50:50, ($M_v$≅80,000 Daltons) 7% and a suitable organic solvent, such as DMSO, are then laid down over the second therapeutic agent layer to provide a cap layer.

Following implantation of the filled stent in vivo, the cap layer degrades allowing the Dexmethasone to be delivered. The protective layer protects the PCN-1 ribozyne from degrading while the Dexamethasone is delivered. After the protective layer degrades, the PCN-1 ribozyme is then delivered.

Example 3

Formulation Comprising a Therapeutic Agent in a Therapeutic Agent Layer and a Protective Layer Containing an Activating Agent

A first mixture of high molecular weight poly(lactide-co-glycolide) (PLGA), lactide:glycolide: 50:50 ($M_v$>100,000 Daltons), 7% wt. and a suitable organic solvent, such as DMSO, 93% wt. is prepared. The mixture is loaded drop-wise into holes in the stent, then the solvent is evaporated to form the barrier layer. A second barrier layer is laid over the first by the same method of filling polymer solution into the hole followed by solvent evaporation. The process is continued until five individual layers have been laid down to form the complete barrier layer.

A second mixture of chymotrypsin, 3% solids basis, and polyvinyl pyrrolidone, 7% solids basis, in a solvent mixture of water:DMSO: 50:50 is introduced into holes in the stent over the barrier layer. The solvent is evaporated to form an activating ester hydrolytic enzyme filled protective layer and the filling and evaporation procedure repeated until the hole is filled to about 20% of its total volume with enzyme in activating layer.

Three layers of a third solution, of poly(lactide-co-glycolide) (PLGA), lactide:glycolide: 50:50, ($M_v$≅80,000 Daltons) 7% wt. and a suitable organic solvent, such as DMSO, are then laid down over the enzyme in matrix layer to provide a time delay.

A fourth solution of a pro-drug paclitaxel-polyglutamic acid (PTX-PGA) conjugate (where a free hydroxyl group on paclitaxel is covalently bonded via an ester linkage to the PGA), 1% wt. and poly(lactide-co-glycolide) (PLGA), lactide:glycolide: 50:50, ($M_v$≅80,000 Daltons) 7% wt. and a suitable organic solvent, such as DMSO, 92% wt. is prepared. The mixture is filled into holes in the stent over the protective layer, then the solvent is evaporated to form the pro-drug layer. A pro-drug layer is laid over the first by the same method of filling polymer solution into the hole followed by solvent evaporation. The process is continued until six individual layers have been laid down to form the pro-drug layer.

Following implantation of the filled stent in vivo, the pro-drug is released first and partitions into the arterial tissue. After a delay time while the protection layer degrades, the protected chymotrypsin is released and enzymatically hydrolyzes the ester bond of the pro-drug to activate release of the drug paclitaxel in the tissue.

Example 4

Formulation Comprising a Therapeutic Agent in a Therapeutic Agent Layer and a Protective Layer Containing a Deactivating Agent

A first mixture of poly-lactide, 5% wt. and a suitable organic solvent, such as DMSO, 95% wt. is prepared. The mixture is loaded drop-wise into holes in the stent, then the solvent is evaporated to form the barrier layer. A second barrier layer is laid over the first by the same method of filling polymer solution into the hole followed by solvent evaporation. The process is continued until five individual layers have been laid down to form the complete barrier layer.

A second mixture of citric acid, 8% solids basis, and polyvinyl pyrrolidone, 2% solids basis, in a solvent mixture of water:DMSO: 50:50 is introduced into holes in the stent over the barrier layer. The solvent is evaporated to form a deactivating compound containing layer capable of catalyzing the hydrolysis of phosphodiester bonds and depolymerizing and deactivating RNA oligomers. The filling and evaporation procedure is repeated until the hole is filled to about 20% of its total volume with enzyme in activating layer.

Three layers of a third solution, of poly(lactide-co-glycolide) (PLGA), lactide:glycolide: 50:50, 7% wt. and a suitable organic solvent, such as DMSO, are then laid down over the deactivating compound containing layer to provide a separating layer by the same fill and evaporate sequence.

A fourth mixture of PCN-1 ribozyme, 8% solids basis, and polyvinyl pyrrolidone, 2% solids basis, in a solvent mixture of water:DMSO: 50:50 is introduced into holes in the stent over the separation layer. The solvent is evaporated to form an anti-sense oligonucleotide filled polymer therapeutic agent layer and the filling and evaporation procedure repeated until the hole is filled to about 20% of its total volume.

A fifth mixture of PLGA lactide:glycolide: 50:50, ($M_v \cong 80,000$ Daltons) 7% and a suitable organic solvent, such as DMSO, are then laid down over the therapeutic agent layer to provide a cap layer.

Following implantation of the filled stent in vivo, the PCN-1 ribozyme is released first and partitions into the arterial tissue and provides a therapeutic effect. After a delay time while the protection layer degrades, the protected citric acid is released and catalytically hydrolyzes the phosphodiester ester bond of ribozyme oligonucleotide backbone and terminates its therapeutic activity.

Example 5

Formulation Comprising a Therapeutic Agent in a Therapeutic Agent Layer and a Protective Layer Containing an Antacid A first mixture of poly(lactide-co-glycolide) (PLGA), lactide:glycolide: 85:15, ($M_v > 100,000$ Daltons) 7% wt. and a suitable organic solvent, such as DMSO, 93% wt. is prepared. The mixture is loaded drop-wise into holes in the stent, then the solvent is evaporated to form the barrier layer. A second barrier layer is laid over the first by the same method of filling polymer solution into the hole followed by solvent evaporation. The process is continued until five individual layers have been laid down to form the complete barrier layer.

A second mixture of sirolimus, 3% solids basis, poly(lactide-co-glycolide) (PLGA), lactide:glycolide: 50:50, ($M_v \cong 80,000$ Daltons) 7% wt, and magnesium hydroxide, 0.35% wt (5% wt based on PLGA) is introduced into holes in the stent over the barrier layer. The solvent is evaporated to form a drug protecting layer containing drug and an antacid and the filling and evaporation procedure repeated until the hole is filled to about 60% of its total volume with protecting layer.

Three layers of a third solution, of poly(lactide-co-glycolide) (PLGA), lactide:glycolide: 50:50, ($M_v \cong 80,000$ Daltons) 7% wt. and a suitable organic solvent, such as DMSO, are then laid down.

A fourth mixture of PLGA lactide:glycolide: 50:50, ($M_v \cong 80,000$ Daltons) 7% and a suitable organic solvent, such as DMSO, are then laid down over the therapeutic agent layer to provide a cap layer.

Following implantation of the filled stent in vivo, PLGA polymer degrades via hydrolysis and sirolimus is released, as well as acidic byproducts (lactic and glycolic acids as well as acid function terminated PLGA oligomers). The acidic byproducts are immediately and continuously neutralized by the action of magnesium hydroxide over the time the sirolimus is released, thus protecting the sirolimus from acid catalyzed degradation.

Example 6

Measurement of Paclitaxel Release Rates from a Medical Device with Multiple Therapeutic Agent Layers A solution of phosphate buffered saline (PBS) is prepared by dissolving five "Phosphate Buffered Saline Tablets" (Sigma-Aldrich Co., catalog #P-4417) in 1000 mL deionized water to provide a solution with a pH of 7.4, 0.01 M in phosphate buffer, 0.0027 M in potassium chloride and 0.137 M in sodium chloride. This PBS solution is used as a Release Solution.

The elution rate of drug from the multilayered stent of Example 1 is determined in a standard sink condition experiment.

A first 10 mL screw capped vial is charged with release solution, 3 mL, then placed in a shaking water bath held at 37° C. until temperature has equilibrated. The above stent containing a drug in matrix layer in between two protection layers is placed into the release solution, shaking at 60 cycles per minute commenced, and the stent is held immersed in the release solution for a period of time. The stent is then placed in a second screw capped vial is charged with release solution, 3 mL, at 37° C., and held for a period of time. The first release solution is called sample #1. From time to time, the stent is removed from release solution in one vial and placed into fresh solution in the next vial to generate a series of samples containing varying amounts of drug eluted from the stent.

The amount of paclitaxel in a given release solution sample is determined by High Pressure Liquid Chromatography (HPLC). The following conditions are used:

Analysis Column: Sym. $C_{18}$ (5 µm, 3.9×150 mm, Waters Corp., MA)

Mobile phase: Water/Acetonitrile: 55% vol./45% vol.

Flow Rate: 1 mL/minute

Temperature: 25° C.

Detection wavelength: 227 nm

Injection volume: 50 µL

Retention time: 10.5 minutes

By comparison with a calibration curve generated from known stock solutions, the amount of paclitaxel eluted into the release solution during any time period of the experiment can be calculated.

Methods and results for measuring release profiles are published in A. Finkelstein et al., "The Conor Medsystems Stent: A programmable Drug Delivery Device," TCT 2001 Conference, Washington, D.C., September 2001.

While the invention has been described in detail with reference to the preferred embodiments thereof, it will be apparent to one skilled in the art that various changes and modifications can be made and equivalents employed, without departing from the present invention.

What is claimed is:

1. An implantable medical device comprising:
   an implantable device body having a plurality of through holes therein;
   a barrier formed in the plurality of through holes, the barrier formed of a biodegradable copolymer having a first copolymer ratio;
   a drug filled portion formed in the plurality of through holes adjacent the barrier; and
   a cap formed in the plurality of through holes adjacent the drug filled portion, the cap formed of the biodegradable copolymer having a second copolymer ratio, wherein the second copolymer ratio is different from the first copolymer ratio, and wherein the barrier is formed adjacent a luminal surface of the implantable device body, the cap is formed adjacent a mural surface of the implantable device body, and the cap degrades faster than the barrier.

2. The device of claim 1, wherein the implantable medical device is a stent.

3. The device of claim 2, wherein the drug filled portion comprises a drug for prevention of restenosis.

4. The device of claim 1, wherein the barrier, the drug filled portion, and the cap are formed by loading compositions dropwise into the through holes.

5. The device of claim 1, wherein the biodegradable copolymer is poly(lactide-co-glycolide).

6. The device of claim 5, wherein the first copolymer ratio is 85:15.

7. The device of claim 5, wherein the second copolymer ratio is 50:50.

8. The device of claim 1, wherein the first and second copolymer ratios are selected such that following implantation the cap degrades faster than the barrier.

9. The device of claim 1, wherein the drug filled portion includes a limus drug.

10. The device of claim 1, wherein the drug filled portion includes a water sensitive drug.

11. A method of forming an implantable medical device comprising:
   forming an implantable device body having a plurality of through holes therein;
   loading a mixture of a biodegradable copolymer having a first copolymer ratio and a first solvent into the holes and evaporating the first solvent to form a barrier;
   loading a mixture of a drug, a polymer, and a second solvent into the holes and evaporating the second solvent to form a drug portion; and
   loading a mixture of the biodegradable copolymer having a second copolymer ratio and a third solvent into the holes and evaporating the third solvent to form a cap, wherein the second copolymer ratio is different from the first copolymer ratio, and wherein the barrier is formed adjacent a luminal surface of the implantable device body, the cap is formed adjacent a mural surface of the implantable device body, and the cap degrades faster than the barrier.

12. The method of claim 11, wherein the first, second, and third solvents are the same.

13. The method of claim 11, wherein the implantable medical device is a stent.

14. The method of claim 11, wherein the drug comprises a drug for prevention of restenosis.

15. The method of claim 11, wherein the loading steps include loading the mixtures dropwise into the through holes.

16. The method of claim 11, wherein the biodegradable copolymer is poly(lactide-co-glycolide).

17. The method of claim 16, wherein the first copolymer ratio is 85:15.

18. The method of claim 16, wherein the second copolymer ratio is 50:50.

19. The method of claim 11, wherein the first and second copolymer ratios are selected such that following implantation the cap degrades faster than the barrier.

20. The method of claim 11, wherein the drug comprises a limus drug.

21. The method of claim 11, wherein the drug comprises a water sensitive drug.

* * * * *